US012790648B2

(12) United States Patent
Yu et al.

(10) Patent No.: US 12,790,648 B2
(45) Date of Patent: Nov. 10, 2026

(54) DNA METHYLATION-RELATED MARKER FOR DIAGNOSING TUMOR, AND APPLICATION THEREOF

(71) Applicant: SHANGHAI PUBLIC HEALTH CLINICAL CENTER, Shanghai (CN)

(72) Inventors: Wenqiang Yu, Shanghai (CN); Shihua Dong, Shanghai (CN)

(73) Assignee: SHANGHAI PUBLIC HEALTH CLINICAL CENTER, Shanghai (CN)

( * ) Notice: Subject to any disclaimer, the term of this patent is extended or adjusted under 35 U.S.C. 154(b) by 1256 days.

(21) Appl. No.: 17/268,268

(22) PCT Filed: Aug. 8, 2019

(86) PCT No.: PCT/CN2019/099722

§ 371 (c)(1),
(2) Date: Jun. 28, 2021

(87) PCT Pub. No.: WO2020/034888

PCT Pub. Date: Feb. 20, 2020

(65) Prior Publication Data

US 2021/0340627 A1 Nov. 4, 2021

(30) Foreign Application Priority Data

Aug. 16, 2018 (CN) ........................ 201810935933.8

(51) Int. Cl.
*C12Q 1/6886* (2018.01)

(52) U.S. Cl.
CPC ..... *C12Q 1/6886* (2013.01); *C12Q 2600/154* (2013.01)

(58) Field of Classification Search
None
See application file for complete search history.

(56) References Cited

U.S. PATENT DOCUMENTS

| | | | | |
|---|---|---|---|---|
| 8,841,268 B2 | 9/2014 | Hiromu et al. | | |
| 9,745,622 B2 | 8/2017 | An et al. | | |
| 2013/0041047 A1 * | 2/2013 | Orntoft ................ | C12Q 1/6886 514/789 | |

FOREIGN PATENT DOCUMENTS

| | | | | |
|---|---|---|---|---|
| CN | 104450872 A | 3/2015 | | |
| CN | 107988366 A | 5/2018 | | |
| JP | 2013509872 A | 3/2013 | | |
| JP | 2014140377 A | 8/2014 | | |
| WO | WO-2014173905 A2 * | 10/2014 | .......... | C12Q 1/6886 |
| WO | WO 2015/155660 A1 | 10/2015 | | |
| WO | WO 2015/191780 A2 | 12/2015 | | |
| WO | WO 2016/115354 A1 | 7/2016 | | |
| WO | WO 2018/111935 A1 | 6/2018 | | |
| WO | WO-2020034888 A1 | 2/2020 | | |

OTHER PUBLICATIONS

NCBI Database GenBank Accession No. AY128659, National Library of Medicine, available via URL: <ncbi.nlm.nih.gov/nuccore/AY128659.1/> (Year: 2002).*
Tao et al PLoS ONE, 6(5): e19862, 11 pages (Year: 2011).*
Sandoval et al. J Clinical Oncology. 31: 4140-4147 and Supplementary Material (Year: 2013).*
Genbank Database Nucleotide, dated Oct. 23, 2002 (Oct. 23, 2002), "*Homo sapiens* clone HIST1H4F histone H4 gene, complete cds," Database Accession No. AY128659.1*,1 page.
Genbank Database Nucleotide, dated Oct. 23, 2002 (Oct. 23, 2002), "*Homo sapiens* clone HIST1H4I histone H4 gene, complete cds," Database Accession No. AY128662.1*, 1 page.
Genbank Database Nucleotide, dated Oct. 23, 2002 (Oct. 23, 2002), "*Homo sapiens* histone H3 (HIST1H3C) gene, complete cds," Database Accession No. AF531276.1*, 1 page.
Genbank Database Nucleotide, dated Jan. 24, 2013 (Jan. 24, 2013), "Human DNA sequence from clone RP1-221C16 on chromosome 6, complete sequence," Database Accession No. AL353759.8*, 20 pages.
Gezer, U., et al., "Histone Methylation Marks on Circulating Nucleosomes as Novel Blood-Based Biomarker in Colorectal Cancer," International Journal of Molecular Sciences 16(12): 29654-29662, MDPI, Switzerland (2015).
International Search Report in International Application No. PCT/CN2019/099722, mailed Nov. 6, 2019, China National Intellectual Property Administration, China, 4 pages.
Genbank, "B.taurus DNA sequence 1 from patent application EP0238993," Accession No. A00002, accessed at https://www.ncbi.nlm.nih.gov/nuccore/2, accessed on Apr. 24, 2022, 1 page.
Behbahani, T.E., et al., "Alterations of global histone H4K20 methylation during prostate carcinogenesis," *BMC Urology* 12:5, Biomed Central, United Kingdom (2012).
Nayak, S.R., et al., "A Role for Histone H2B Variants in Endocrine-Resistant Breast Cancer", Hormones and Cancer, 6(5-6):214-24, Springer Science+Business Media, United States (Dec. 2015).
Lindqvist, B., et al., "Whole genome DNA methylation signature of HER2-positive breast cancer", Epigenetics, 9(8):1149-62, Taylor & Francis, United Kingdom (Jul. 2014).
Citrus, "DNA Methylation Profile Study Related to Diagnosis and Prognosis of Hepatitis B Liver Cancer", The Full Database (Dr.) Health Science Series of Mag Thesis, Good Bung, China, 2009 (2012) E072-102, publication date Sep. 15, 2012.
Zhang, et al., "Research on Prevention and Treatment of Gastric Cancer: S100A6 May Serve as a Biomarker for Gastric Cancer", Basic Oncology—The 18th branch of the 13th China Association for Science and Technology Annual Conference; Sep. 21-22, 2011, Sep. 21, 2011; Sep. 21, 2011-Sep. 22, 2011 China Association for Science and Technology, CN.

(Continued)

*Primary Examiner* — Carla J Myers
(74) *Attorney, Agent, or Firm* — STERNE, KESSLER, GOLDSTEIN & FOX P.L.L.C.

(57) ABSTRACT

Provided are DNA methylation related markers for diagnosis of tumors and application thereof. Disclosed are gene sequence regions having abnormal DNA methylation in the genome, named tumor markers CTSM-4F, CTSM-2BE, CTSM-3C, CTSM-4I. The methylation levels of those sequence regions are significantly different between tumor tissues and non-tumor tissues, with their CpG(s) hypermethylated in tumor tissues.

2 Claims, 5 Drawing Sheets

Specification includes a Sequence Listing.

(56) References Cited

OTHER PUBLICATIONS

Dong, S., et al., "Histone-Related Genes are Hypermethylated in Lung Cancer and Hypermethylated HIST1H4F Could Serve as a Pan-Cancer Biomarker," Cancer Research 79(24):6101-6112, American Association for Cancer Research, United States (Dec. 2019).
Fraga, M.F., et al., "Loss of acetylation at Lys16 and trimethylation at Lys20 of histone H4 is a common hallmark of human cancer," Nat Genet 37(4):391-400, Springer Nature, Germany (Apr. 2005).
GenBank, "*Homo sapiens* histone H2B (HIST1H2BE) gene, complete cds," Accession No. AF531288.1, accessed at https://www.ncbi.nlm.nih.gov/nuccore/AF531288, accessed on Jun. 30, 2025, 2 pages.
Mishra, N.K., and Guda, C., "Genome-wide DNA Methylation Analysis Reveals Molecular Subtypes of Pancreatic Cancer," Oncotarget 8(17):28990-29012, Impact Journals, United States (Apr. 2017).
Olaru, A.V., et al., "Unique patterns of CpG island methylation in inflammatory bowel disease-associated colorectal cancers," Inflamm Bowel Dis 18(4):641-648, Oxford University Press, United Kingdom (Apr. 2012).

* cited by examiner

SEQUENCE LISTING

<160> NUMBER OF SEQ ID NOS: 21

<210> SEQ ID NO 1
<211> LENGTH: 699
<212> TYPE: DNA
<213> ORGANISM: Homo sapiens

<400> SEQUENCE: 1

```
cgcccagtaa gttacggaaa aggcggagac agaggtttcg ttcccgcccc tccaattcag     60

tctccaaaaa ggtccgcata attgatatat aaggggcttc agtgtgtagc aaagttgcaa    120

aagttaagag ttgttgtttg tcttcgatca tgtctggtag aggcaaaggt ggtaaaggtt    180

taggaaaggg aggcgccaag cgccatcgca aagtgctgcg tgacaacata cagggcatca    240

cgaagcccgc catccgtcgc ttggcccgac gcggcggcgt gaaacgcatt tcgggcctca    300

tttatgagga gacccgcggt gttcttaagg tgttcctgga gaatgtgata cgggacgccg    360

taacctacac ggagcacgcc aagcgtaaga cagtcactgc aatggatgtt gtctacgcgc    420

tcaagcgcca gggacgcact ctgtacggct ttggtggctg agcctcaccc cggcttttta    480

tttaacagct cacccataaa aggccctttt cagggccacc tccttcgtca cacgaagggc    540

tgtaactgat gacgacttgg gtttcgtttt gtaaatttgg gattctaact gagttaaacc    600

gagccgtttt tagcgatctt cctaagatgg cggatgtgct aaggagaaag ggaaggcgaa    660

acattagaaa cttgttcagg tatttcgatc gcaaacatt                           699
```

<210> SEQ ID NO 2
<211> LENGTH: 699
<212> TYPE: DNA
<213> ORGANISM: Artificial Sequence
<220> FEATURE:
<223> OTHER INFORMATION: Polynucleotide
<220> FEATURE:
<221> NAME/KEY: misc_feature
<222> LOCATION: (1)..(699)
<223> OTHER INFORMATION: bisulfite treated sequence
<220> FEATURE:
<221> NAME/KEY: misc_feature
<222> LOCATION: (1)..(699)
<223> OTHER INFORMATION: y is c or t

<400> SEQUENCE: 2

```
ygtttagtaa gttayggaaa aggyggagat agaggtttyg ttttygtttt tttaatttag     60

tttttaaaaa ggttygtata attgatatat aaggggtttt agtgtgtagt aaagttgtaa    120

aagttaagag ttgttgtttg ttttygatta tgtttggtag aggtaaaggt ggtaaaggtt    180

taggaaaggg aggygttaag ygttatygta aagtgttgyg tgataatata tagggtatta    240

ygaagttygt tattygtygt ttggttygay gyggyggygt gaaaygtatt tygggtttta    300

tttatgagga gattygyggt gtttttaagg tgtttttgga gaatgtgata ygggaygtyg    360

taatttatay ggagtaygtt aagygtaaga tagttattgt aatggatgtt gtttaygygt    420

ttaagygtta gggaygtatt ttgtayggtt ttggtggttg agttttattt yggtttttta    480

tttaatagtt tatttataaa aggttttttt tagggttatt tttttygtta taygaagggt    540

tgtaattgat gaygatttgg gtttygtttt gtaaatttgg gattttaatt gagttaaaty    600

gagtygtttt tagygatttt tttaagatgg yggatgtgtt aaggagaaag ggaaggygaa    660

atattagaaa tttgtttagg tatttygaty gtaaatatt                           699
```

<210> SEQ ID NO 3
<211> LENGTH: 624

```
<212> TYPE: DNA
<213> ORGANISM: Homo sapiens

<400> SEQUENCE: 3

agctgtttgt taaataggct ttcattttaa ttttttaaaa aatattttca ctagttagac      60

ggaatattta tttctgatcc tcgttgtagg gctaaactag gtgtgacttg cttttccatt     120

aaggactgta gccattttgg ctaagaaagt ctttcctgtc ttagctctct tcaagagatg     180

ctatttactt ttttgttgtt gttttctccg gagctttatt gcctaccctt tattttcacg     240

atgtgtttgt gcattctgta aaaagtggga aacactgttc tccggattgt gtgggtgatc     300

gccggtcgcc tagcttgccg ttcttcaggt atctcctgct gctccagaat ctacatctga     360

atgtcaaggc atagcttttc caggagcttt taaaccgacc tttcaattcg aagacgtaac     420

tgcgccagga gctttgtctc cctggcatat aaaagcatag aagagagcaa cttctggttt     480

ttaaaataag taaactaatc tgaattgttt gcaatggtag gaacttgtta tataaaatgt     540

taattaggtg gcccgtgctc gaaaactgct ctcaggatat gaccaatggg agagtagacc     600

taagctcctt catttgcatg caga                                            624


<210> SEQ ID NO 4
<211> LENGTH: 624
<212> TYPE: DNA
<213> ORGANISM: Artificial Sequence
<220> FEATURE:
<223> OTHER INFORMATION: Polynucleotide
<220> FEATURE:
<221> NAME/KEY: misc_feature
<222> LOCATION: (1)..(624)
<223> OTHER INFORMATION: bisulfite treated sequence
<220> FEATURE:
<221> NAME/KEY: misc_feature
<222> LOCATION: (1)..(624)
<223> OTHER INFORMATION: y is c or t

<400> SEQUENCE: 4

agttgtttgt taaataggtt tttattttaa ttttttaaaa aatattttta ttagttagay      60

ggaatattta tttttgattt tygttgtagg gttaaattag gtgtgatttg ttttttttatt    120

aaggattgta gttattttgg ttaagaaagt tttttttgtt ttagtttttt ttaagagatg     180

ttatttattt ttttgttgtt gtttttttyg gagttttatt gtttattttt tatttttayg     240

atgtgtttgt gtattttgta aaaagtggga aatattgttt ttyggattgt gtgggtgaty     300

gtyggtygtt tagtttgtyg ttttttaggt atttttttgtt gttttagaat ttatatttga    360

atgttaaggt atagtttttt taggagtttt taaatygatt ttttaattyg aagaygtaat     420

tgygttagga gttttgtttt tttggtatat aaaagtatag aagagagtaa tttttggttt     480

ttaaaataag taaattaatt tgaattgttt gtaatggtag gaatttgtta tataaaatgt     540

taattaggtg gttygtgtty gaaaattgtt tttaggatat gattaatggg agagtagatt     600

taagtttttt tatttgtatg taga                                            624


<210> SEQ ID NO 5
<211> LENGTH: 669
<212> TYPE: DNA
<213> ORGANISM: Homo sapiens

<400> SEQUENCE: 5

tggggcaact catccaataa gattgtctag taatgaacca atcagtctgg tcactcttca      60

gccaatgatt ttatcgcgcg ggacttttga aatattacag gaccaatcag aatgtttctc     120
```

```
actatattta aaggccactt gctctcagtt cactacactt ttgtgtgtgc tctcattgca    180

aatggctcgt acgaagcaaa cagctcgcaa gtctaccggc ggcaaagctc cgcgcaagca    240

gcttgctact aaagcagccc gtaagagcgc tccggccacc ggtggcgtga agaaacctca    300

tcgctaccgc ccgggcaccg tggccttgcg cgaaatccgt cgctaccaga agtccaccga    360

gctgctgatc cggaagctgc cgttccagcg cctggtgcga gaaatcgccc aggacttcaa    420

aaccgacctg cgtttccaga gctctgcggt gatggcgctg caggaggctt gtgaggccta    480

cctggtggga ctcttcgaag acaccaatct gtgcgctatt cacgctaaac gcgtcaccat    540

catgcccaaa gatatccagc tggcacgtcg catccgtggg gaaagggcat aagtctgccc    600

gtttcttcct cattgaaaag gctcttttca gagccactca caatttcact taaaaacagt    660

tgtaaccca                                                            669
```

<210> SEQ ID NO 6
<211> LENGTH: 669
<212> TYPE: DNA
<213> ORGANISM: Artificial Sequence
<220> FEATURE:
<223> OTHER INFORMATION: Polynucleotide
<220> FEATURE:
<221> NAME/KEY: misc_feature
<222> LOCATION: (1)..(669)
<223> OTHER INFORMATION: bisulfite treated sequence
<220> FEATURE:
<221> NAME/KEY: misc_feature
<222> LOCATION: (1)..(669)
<223> OTHER INFORMATION: y is c or t

<400> SEQUENCE: 6

```
tggggtaatt tatttaataa gattgtttag taatgaatta attagtttgg ttatttttta     60

gttaatgatt ttatygygyg ggatttttga aatattatag gattaattag aatgtttttt    120

attatattta aaggttattt gtttttagtt tattatattt ttgtgtgtgt ttttattgta    180

aatggttygt aygaagtaaa tagttygtaa gtttatyggy ggtaaagttt ygygtaagta    240

gtttgttatt aaagtagtty gtaagagygt ttyggttaty ggtggygtga agaaatttta    300

tygttatygt tygggtatyg tggttttgyg ygaaattygt ygttattaga agtttatyga    360

gttgttgatt yggaagttgt ygttttagyg tttggtgyga gaaatygttt aggattttaa    420

aatygatttg ygtttttaga gttttgyggt gatggygttg taggaggttt gtgaggttta    480

tttggtggga tttttygaag atattaattt gtgygttatt taygttaaay gygttattat    540

tatgtttaaa gatatttagt tggtaygtyg tattygtggg gaaagggtat aagtttgtty    600

gttttttttt tattgaaaag gttttttttta gagttattta taattttatt taaaaatagt    660

tgtaattta                                                            669
```

<210> SEQ ID NO 7
<211> LENGTH: 374
<212> TYPE: DNA
<213> ORGANISM: Homo sapiens

<400> SEQUENCE: 7

```
tacccataaa agaaagctgc catcacaggc agcagacctt tgttctctga ccacttgata     60

atgtcaggac gcggcaaagg aggtaagggc ctggggaaag ggggtgccaa gcgccaccgc    120

aaggtgctgc gcgacaacat ccagggtatc accaagccag ccattcggcg ccttgctcgc    180

cgcggcggcg tgaagcgcat ttctggcctc atctatgagg agacccgcgg agtgttgaag    240

gtgttcctgg agaacgtgat ccgggacgcc gtgacctaca cggagcacgc caagcgcaag    300
```

acggtcaccg ccatggacgt ggtctacgcg ctcaagcgcc agggccgcac cctctatggc 360
ttcggcggct aaat 374

<210> SEQ ID NO 8
<211> LENGTH: 374
<212> TYPE: DNA
<213> ORGANISM: Artificial Sequence
<220> FEATURE:
<223> OTHER INFORMATION: Polynucleotide
<220> FEATURE:
<221> NAME/KEY: misc_feature
<222> LOCATION: (1)..(448)
<223> OTHER INFORMATION: bisulfite treated sequence
<220> FEATURE:
<221> NAME/KEY: misc_feature
<222> LOCATION: (1)..(448)
<223> OTHER INFORMATION: y is c or t

<400> SEQUENCE: 8
tatttataaa agaaagttgt tattataggt agtagatttt tgtttttga ttatttgata 60 atgttaggay gyggtaaagg aggtaagggt ttggggaaag ggggtgttaa gygttatygt 120
aaggtgttgy gygataatat ttagggtatt attaagttag ttattyggyg ttttgttygt 180
ygyggyggyg tgaagygtat ttttggtttt atttatgagg agattygygg agtgttgaag 240
gtgtttttgg agaaygtgat tygggaygty gtgatttata yggagtaygt taagygtaag 300
ayggttatyg ttatggaygt ggtttaygyg tttaagygtt agggtygtat tttttatggt 360
ttyggyggtt aaat 374

<210> SEQ ID NO 9
<211> LENGTH: 27
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(27)
<223> OTHER INFORMATION: Primer

<400> SEQUENCE: 9
gtagaggtaa aggtggtaaa ggtttag 27

<210> SEQ ID NO 10
<211> LENGTH: 50
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(50)
<223> OTHER INFORMATION: Primer

<400> SEQUENCE: 10
aaccttcaac accccaacca tataaaaaca ccrcraatct cctcataaat 50

<210> SEQ ID NO 11
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(26)

<223> OTHER INFORMATION: Primer

<400> SEQUENCE: 11
tgttgygtga taatatatag ggtatt 26

<210> SEQ ID NO 12
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(24)
<223> OTHER INFORMATION: Primer

<400> SEQUENCE: 12
aaccttcaac accccaacca tata 24

<210> SEQ ID NO 13
<211> LENGTH: 28
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(28)
<223> OTHER INFORMATION: Primer

<400> SEQUENCE: 13
gatgtgtttg tgtattttgt aaaaagtg 28

<210> SEQ ID NO 14
<211> LENGTH: 51
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(51)
<223> OTHER INFORMATION: Primer

<400> SEQUENCE: 14
aaccttcaac accccaacca tatatatacc ttaacattca aatataaatt c 51

<210> SEQ ID NO 15
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(20)
<223> OTHER INFORMATION: Primer

<400> SEQUENCE: 15
ttttyggatt gtgtgggtga 20

<210> SEQ ID NO 16
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(30)
<223> OTHER INFORMATION: Primer

<400> SEQUENCE: 16
tttgttttta gtttattata tttttgtgtg 30

<210> SEQ ID NO 17
<211> LENGTH: 50
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(50)
<223> OTHER INFORMATION: Primer

<400> SEQUENCE: 17
aaccttcaac accccaacca tataaactac tttaataaca aactacttac 50

<210> SEQ ID NO 18
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(23)
<223> OTHER INFORMATION: Primer

<400> SEQUENCE: 18
gtgtgtgttt ttattgtaaa tgg 23

<210> SEQ ID NO 19
<211> LENGTH: 28
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(28)
<223> OTHER INFORMATION: Primer

<400> SEQUENCE: 19
gggtgttaag ygttatygta aggtgttg 28

<210> SEQ ID NO 20
<211> LENGTH: 50
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(50)
<223> OTHER INFORMATION: Primer

<400> SEQUENCE: 20
aaccttcaac accccaacca tatactcctc ataaataaaa ccaaaaatac 50

<210> SEQ ID NO 21
<211> LENGTH: 24
<212> TYPE: DNA
<213> ORGANISM: Artificial Sequence
<220> FEATURE:
<223> OTHER INFORMATION: Primer
<220> FEATURE:

```
<221> NAME/KEY: misc_feature
<222> LOCATION: (1)..(24)
<223> OTHER INFORMATION: Primer

<400> SEQUENCE: 21

tttagggtat tattaagtta gtta                                          24
```

DNA METHYLATION-RELATED MARKER FOR DIAGNOSING TUMOR, AND APPLICATION THEREOF

REFERENCE TO A SEQUENCE LISTING SUBMITTED ELECTRONICALLY VIA EFS-WEB

The content of the electronically submitted sequence listing in ASCII text file (Name: 4792_0010001_Seqlisting_ST25; Size: 11,499 bytes; and Date of Creation: Jun. 22, 2021) is herein incorporated by reference in its entirety.

FIELD OF DISCLOSURE

The disclosure relates to the field of diagnosis. More specifically, the disclosure relates to a DNA methylation related marker for diagnosing of tumor and application thereof.

BACKGROUND OF DISCLOSURE

With the development of tumor research, more and more evidences in the art show that small changes in epigenetic regulation have an important role in tumor.

Epigenetics is a subject that studies that the heritable change of gene function without a change of DNA sequence, which eventually leads to the change of phenotype. Epigenetics mainly includes DNA methylation, histone modification, microRNA level changes and other biochemical processes. DNA methylation refers to the process of transferring methyl from S-adenosylmethionine (methyl donor) to specific bases under the catalysis of DNA methyltransferase. DNA methylation can occur at N-6 of adenine, N-4 of cytosine, N-7 of guanine or C-5 of cytosine. However, DNA methylation in mammals mainly occurs at the C of 5'-CpG-3', which results in 5-methylcytosine (5mC).

More than 98% of CpG dinucleotides are scattered in repetitive sequences with transcription dependent transposition potential. In normal cells, these CPGs are hypermethylated/transcriptionally silenced. While in tumor cells, they undergo extensive demethylation, leading to transcription of repetitive sequences, activation of transposons, high genomic instability and enhanced transcription of protooncogenes. The remaining 2% of the total CpGs was densely distributed in smaller areas (CpG islands). About 40%-50% of the gene promoter regions have CpG islands, suggesting that DNA methylation may be involved in the transcriptional regulation of these genes. In some tumors, these CpG islands, which were hypomethylated in normal cells, will be hypermethylated, leading to inactivation of gene transcription. The affected genes include DNA repair genes, cell-cycle control genes and anti-apoptosis genes.

In view of the high false positive and false negative of tumor markers commonly used in clinic, such as alpha fetoprotein (AFP), it is urgent to develop new markers in this art. It is a new way to study tumor biomarkers by abnormal DNA methylation profile of tumor cells. However, it needs a lot of research and long-term gene identification and comparison of a large number of patients in order to find the abnormal methylation profile that are really related to a tumor.

SUMMARY OF DISCLOSURE

The object of the disclosure is to provide DNA methylation related markers for diagnosing tumor and application thereof.

The first aspect of the present disclosure provides an isolated polynucleotide, comprising:

(a) the polynucleotide with the nucleotide sequence shown in SEQ ID NO: 1;

(b) the polynucleotide with the nucleotide sequence shown in SEQ ID NO: 3;

(c) the polynucleotide with the nucleotide sequence shown in SEQ ID NO: 5;

(d) the polynucleotide with the nucleotide sequence shown in SEQ ID NO: 7;

(e) a fragment of the polynucleotide of (a)-(d), having at least one (such as 2-40, more specifically 3, 5, 8, 10, 15, 20, 25, 30, 35) CpG site with modification; and/or (f) a nucleic acid (antisense strand) complementary to the polynucleotide or fragment of (a)-(e).

In a preferable embodiment, the modification includes 5-methylation (5mC), 5-hydroxymethylation (5hmC), 5-formylcytosine (5fC) or 5-carboxylcytosine (5-caC).

Another aspect of the disclosure provides an isolated polynucleotide, which is converted from the polynucleotide, and as compared with any sequence of the above (a)-(e), its cytosine C of the CpG site(s) with modification is unchanged, and the unmodified cytosine is converted into T(U).

In a preferable embodiment, it is converted from the polynucleotide corresponding to the above (a)-(e) by bisulfate treatment.

In another preferable embodiment, the polynucleotide comprises:

(g) the polynucleotide with the nucleotide sequence shown in SEQ ID NO: 2;

(h) the polynucleotide with the nucleotide sequence shown in SEQ ID NO: 4;

(i) the polynucleotide with the nucleotide sequence shown in SEQ ID NO: 6;

(j) the polynucleotide with the nucleotide sequence shown in SEQ ID NO: 8;

(k) a fragment of the polynucleotide of (g)-(j), having at least one (such as 2-40, more specifically 3, 5, 8, 10, 15, 20, 25, 30, 35) CpG site with modification.

Another aspect of the disclosure provides a use of any polynucleotide described above in manufacture of a tumor detection agent or kit.

In a preferable embodiment, the tumors include: digestive system tumors such as esophageal cancer, gastric cancer, colorectal cancer, liver cancer, pancreatic cancer, bile duct and gallbladder cancer; respiratory system tumors such as lung cancer, pleuroma; hematologic cancers such as leukemia, lymphoma, multiple myeloma; gynecological and reproductive system tumors such as breast cancer, ovarian cancer, cervical cancer, vulvar cancer, testicular cancer, prostate cancer, penile cancer; nervous system tumors such as glioma, neuroblastoma, meningioma; head and neck tumors such as oral cancer, tongue cancer, laryngeal cancer, nasopharyngeal cancer; urinary system tumors such as kidney cancer, bladder cancer, skin and other systems tumors such as skin cancer, melanoma, osteosarcoma, liposarcoma, thyroid cancer.

Another aspect of the disclosure provides a method of preparing a tumor detection agent, including: providing any polynucleotide (such as 1, 2, 3, or 4) described above, designing a detection agent for specifically detecting a target sequence which is the full length or fragment of the polynucleotide; wherein, the target sequence has at least one (such as 2-40, more specifically, 3, 5, 8, 10, 15, 20, 25, 30, 35) modified CpG site; preferably, the detection agent includes (but is not limited to) a primer, a probe.

Another aspect of the disclosure provides an agent or a combination of agents which specifically detect a target sequence, which is the full length or fragment of any of the polynucleotides described above and has at least one (such as 2-40, more specifically, 3, 5, 8, 10, 15, 20, 25, 30, 35) modified CpG site; preferably, the detection agent includes (but is not limited to) a primer, a probe.

In a preferable embodiment, the polynucleotide is the polynucleotide of the nucleotide sequence shown in SEQ ID NO: 1, and the target sequence contains the fragment of residues 240-296 of SEQ ID NO:1; preferably, the primer is as shown in SEQ ID NO: 9-12.

In another preferable embodiment, the polynucleotide is the polynucleotide of the sequence shown in SEQ ID NO: 3, and the target sequence contains the fragment of residues 279-323 of SEQ ID NO:3; preferably, the primer is as shown in SEQ ID NO: 12-15; or In another preferable embodiment, the polynucleotide is the polynucleotide of the sequence shown in SEQ ID NO: 5, and the target sequence contains the fragment of residues 186-235 of SEQ ID NO:5; preferably, the primer is as shown in SEQ ID NO: 12, 16-18; or In another preferable embodiment, the polynucleotide is the polynucleotide of the sequence shown in SEQ ID NO: 7, and the target sequence contains the fragment of residues 164-198 of SEQ ID NO:7; preferably, the primer is as shown in SEQ ID NO: 12, 19-21.

Another aspect of the disclosure provides the use of the agent or combination of agents in the manufacture of a kit for detecting tumors; preferably, the tumors comprise: digestive system tumors such as esophageal cancer, gastric cancer, colorectal cancer, liver cancer, pancreatic cancer, bile duct and gallbladder cancer; respiratory system tumors such as lung cancer, pleuroma; hematologic cancers such as leukemia, lymphoma, multiple myeloma; gynecological and reproductive system tumors such as breast cancer, ovarian cancer, cervical cancer, vulvar cancer, testicular cancer, prostate cancer, penile cancer; nervous system tumors such as glioma, neuroblastoma, meningioma; head and neck tumors such as oral cancer, tongue cancer, laryngeal cancer, nasopharyngeal cancer; urinary system tumors such as kidney cancer, bladder cancer, skin and other systems tumors such as skin cancer, melanoma, osteosarcoma, liposarcoma, thyroid cancer.

Another aspect of the present disclosure provides a detection kit, comprising container(s) and the agent or combination of agents described above in the container(s); preferably, each agent is located in an independent container.

In a preferable embodiment, the kit also includes: bisulfite, DNA purification agent, DNA extraction agent, PCR amplification agent and/or instruction for use (indicating operation steps of the detection and a result judgment standard).

In another aspect of the disclosure, a method of detecting the methylation profile of the polynucleotide or a fragment thereof in a sample in vitro is provided, comprising:

(i) providing the sample and extracting DNA;

(1) treating the sample to be detected to convert the unmodified cytosine into uracil; preferably, the modification includes 5-methylation (5mC), 5-hydroxymethylation (5hmC), 5-formylcytosine-modified (5fC) or 5-carboxylcytosine-modified (5-caC); preferably, treating the DNA of step (i) with bisulfite;

(iii) analyzing the modification of the polynucleotide or a fragment thereof in the genomic DNA treated by step (ii).

In a preferable embodiment, the abnormal methylation profile is the high level of methylation of C in CPG(s) of the polynucleotide.

In another preferable embodiment, the methylation profile detecting method is not for the purpose of directly obtaining the diagnosis result of a disease, or is not a diagnostic method.

In another preferable embodiment, in step (3), the analysis methods include (but are not limited to): pyrosequencing, bisulfite conversion sequencing, qPCR, second generation sequencing, whole genome methylation sequencing, DNA enrichment detection, simplified bisulfate sequencing technology, HPLC, or their combination.

Other aspects of the disclosure will be apparent to those skilled in the art based on the disclosure herein.

DETAILED DESCRIPTION

Figure 1:
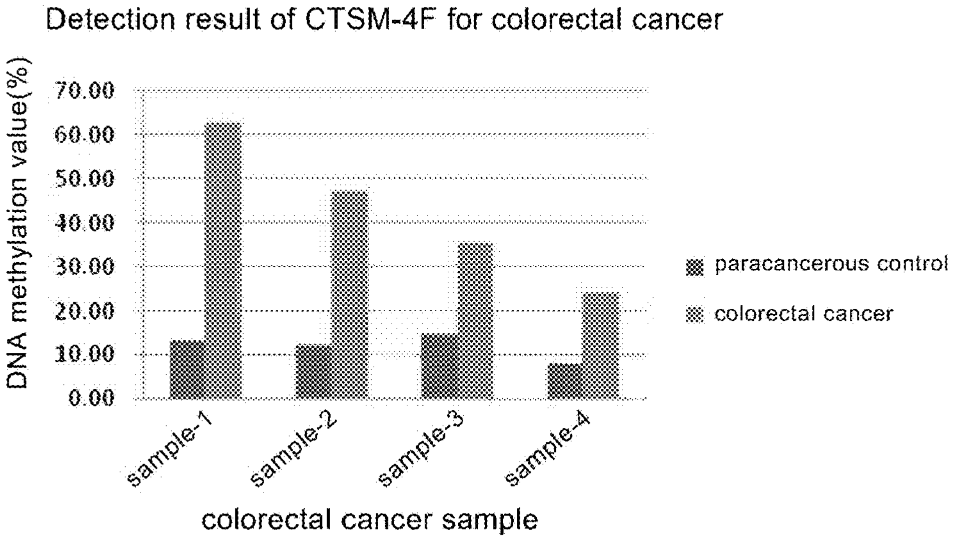
FIG. 1. Detection results of CTSM-4F for colorectal cancer.

The inventor is committed to the research of tumor markers. After extensive research and screening, gene sequence regions with abnormal DNA methylation in the genome have been identified and named as tumor markers CTSM-4F, CTSM-2BE, CTSM-3C and CTSM-4I. Clinical studies show that the methylation status of these regions is significantly different between a tumor tissue and a non-tumor tissue, i.e., their CpG(s) was hypermethylated. Therefore, these genes are tumor markers and can be used as the basis of designing tumor diagnostic agents.

Term

As used herein, "isolated" refers to a material separated from its original environment (if the material is a natural material, the original environment is the natural environment). For example, in living cells, polynucleotides and polypeptides in their natural state are not isolated or purified, but the same polynucleotides or polypeptides will be isolated ones if they are separated from other substances existed in the natural state.

As used herein, "sample" includes substances suitable for DNA methylation detection obtained from any individual or isolated tissue, cell or body fluid.

As used herein, "hypermethylation" refers to high level of methylation, hydroxymethylation, formylcytosine-modified or carboxylcytosine-modified of CpG in a gene sequence. For example, in the case of methylation specific PCR (MSP), if the PCR reaction with methylation specific primers has positive PCR results, the DNA (gene) region of interest is in hypermethylation state. For another example, in the case of real-time quantitative methylation specific PCR, hypermethylation can be determined based on statistic difference of the methylation status value as compared with the control sample.

As used herein, the tumors include but are not limited to: digestive system tumors such as esophageal cancer, gastric cancer, colorectal cancer, liver cancer, pancreatic cancer, bile duct and gallbladder cancer; respiratory system tumors such as lung cancer, pleuroma; hematologic cancers such as leukemia, lymphoma, multiple myeloma; gynecological and reproductive system tumors such as breast cancer, ovarian cancer, cervical cancer, vulvar cancer, testicular cancer, prostate cancer, penile cancer; nervous system tumors such as glioma, neuroblastoma, meningioma; head and neck tumors such as oral cancer, tongue cancer, laryngeal cancer, nasopharyngeal cancer; urinary system tumors such as kidney cancer, bladder cancer, skin and other systems tumors such as skin cancer, melanoma, osteosarcoma, liposarcoma, thyroid cancer.

Gene Marker

In order to find a useful target for tumor diagnosis, the inventor has found a group of gene sequence regions after extensive and in-depth research, which are CTSM-4F, CTSM-2BE, CTSM-3C and CTSM-4I. The methylation status of the sequence of these genes is significantly different between a tumor tissue and a non-tumor tissue. If abnormal methylation (hypermethylation) is detected in the promoter region of one of the above genes, the subject can be identified as having a high-risk of tumor.

Therefore, the disclosure provides an isolated polynucleotide of the human genome, comprising the nucleotide sequence shown in the sequence of SEQ ID NO: 1, 3, 5, or 7. For tumor cells from the patient, the polynucleotide contains 5-methylcytosine (5mC) at C positions of many 5'-CpG-3'. The disclosure also comprises a fragment of the polynucleotide of the sequence shown in SEQ ID NO: 1, 3, 5 or 7, having at least one (such as 2-40, more specifically 3, 5, 8, 10, 15, 20, 25, 30, 35) methylated CpG site. The above polynucleotides or fragments or complementary chains (antisense chains) can also be used in the design of detection agents or detection kits.

The above polynucleotides can be used as the key regions for analysis of the methylation status in the genome. Their methylation status can be analyzed by various technologies known in the art. Any technique that can be used to analyze the methylation state can be applied to the present disclosure.

When treated with bisulfite, un-methylated cytosine(s) of the above polynucleotides will be converted into uracil, while methylated cytosine(s) remained unchanged.

Therefore, the disclosure also provides the polynucleotides obtained from the above polynucleotides (including the complementary chain (antisense chain)) after being treated with bisulfite, including the polynucleotides of the sequence shown in SEQ ID NO: 2, 4, 6, or 8. These polynucleotides can also be used in the design of detection agents or detection kits.

The disclosure also comprises a fragment of the polynucleotides obtained from the above polynucleotides (including their complementary chains (antisense chains)) or the antisense chain thereof after being treated with bisulfite, wherein the fragment contains at least one methylated CpG site.

Detection Agents and Kits

Based on the new discovery of the disclosure, a detection agent designed based on said polynucleotide(s) is also provided for detecting the methylation profile of polynucleotide(s) in the sample in vitro. The detection methods and agents known in the art for determining the sequence and methylation of the genome can be applied in the disclosure.

Therefore, the disclosure provides a method of preparing a tumor detection agent, including: providing the polynucleotide(s) (1, 2, 3 or 4 of the polynucleotides), designing a detection agent for specifically detecting a target sequence which is the full length or fragment of the polynucleotide; wherein, the target sequence has at least one methylated CpG site.

In a preferable embodiment, the target sequence comprises the nucleotide fragment of residues 240-296 of SEQ ID NO: 1; the nucleotide fragment of residues 279-323 of SEQ ID NO: 3; the nucleotide fragment of residues 186-235 of SEQ ID NO: 5; preferably, the primers are as shown in SEQ ID NO: 12, 16-18; or comprises the nucleotide fragment of residues 164-198 of SEQ ID NO: 7.

The detection agent includes but is not limited to: a primer, a probe, etc.

For example, the agent is a primer pair. Based on the sequence of the polynucleotide, those skilled in the art know how to design primer(s). The two primers are on each side of the specific sequence of the target gene to be amplified (including CpG sequence, for the gene region originally methylated, the primer is complementary with CpG, and for the gene region originally un-methylated, the primer is complementary with TpG).

The agent can also be a combination of agents (primer combination), including more than one set of primers, so that the multiple polynucleotides can be amplified respectively.

In a preferred embodiment of the disclosure, the primers are as shown in SEQ ID NO: 9-12; or as shown in SEQ ID NO: 12-15; or as shown in SEQ ID NO: 12, 16-18; or as shown in SEQ ID NO: 12, 19-21. These primers are used for nested PCR, and the amplified products after two runs of PCR are used for sequence identification. The products amplified by the above primers have suitable length and high specificity, even for the amplification of a complex system. These primers are especially suitable for methylation-specific PCR.

The disclosure also provides a kit for detecting the methylation profile of polynucleotide in a sample in vitro, which comprises container(s) and the above primer pair(s) in the container(s).

In addition, the kit can also include various reagents required for DNA extraction, DNA purification, PCR amplification, etc.

In addition, the kit can also include an instruction for use, which indicates operation steps of the detection and a result judgment standard, for the application of those skilled in the art.

Detection Method

The methylation profile of a polynucleotide can be determined by any technique in the art (such as methylation specific PCR (MSP) or real-time quantitative methylation specific PCR, Methylight), or other techniques that are still developing and will be developed.

Quantitative methylation specific PCR (QMSP) can also be used to detect methylation level. It is a continuous optical monitoring method based on fluorescent PCR, which is more sensitive than MSP. It has high throughput and avoids electrophoresis based result analysis.

Other available technologies include conventional methods in the art such as pyrosequencing, bisulfite conversation sequencing, qPCR, second generation sequencing, whole genome methylation sequencing, DNA enrichment detection, simplified bisulfite sequencing or HPLC, and combined gene group detection. It should be understood that, on the basis of the new disclosure herein, these well-known technologies and some technologies to be developed in the art can be applied to the present disclosure.

As a preferable embodiment of the disclosure, a method of detecting the methylation profile of a polynucleotide in a sample in vitro is also provided. The method is based on the follow principle: the un-methylated cytosine can be converted into uracil by bisulfite, which can be transformed into thymine in the subsequent PCR amplification process, while the methylated cytosine remains unchanged; therefore, after the polynucleotide is treated by bisulfite, the methylated site presents a polynucleotide polymorphism (SNP) similar to C/T. Based on the above principle, methylated and un-methylated cytosine can be distinguished by identifying the methylation profile of a polynucleotide in the sample.

The method of the disclosure includes: (a) providing samples and extracting genomic DNA; (b) treating the genomic DNA of step (a) with bisulfite, so as to convert the un-methylated cytosine in the genomic DNA into uracil; (c) analyzing whether the genomic DNA treated in step (b) contains an abnormal methylation profile.

The method of the disclosure can be used for: (i) analyzing whether a subject suffering from tumor by detecting the sample of the subject; (ii) identifying a high-risk population for tumor. The method may also be a case in which the purpose is not to obtain a direct disease diagnosis results.

In a preferable embodiment of the disclosure, DNA methylation is detected by PCR amplification and pyrosequencing. It should be understood by those in the art that DNA methylation detection is not limited to these methods, and any other DNA methylation detection method can also be used. The primers used in PCR amplification are not limited to those provided in Examples.

In a preferable embodiment of the disclosure, because of bisulfite treatment, in which un-methylated cytosine in genomic DNA are converted into uracil and then transformed into thymine in the subsequent PCR process, the sequence complexity of the genome will be reduced, and it will be more difficult to amplify specific target fragments by PCR. The inventor has found that, nested PCR can improve amplification efficiency and specificity, wherein two sets of primers (outer primers and inner primers) are used in two successive runs of PCR, and the product from the first run undergoes a second run with the second set of primers. It should be understood that the detection methods suitable for the present disclosure are not limited thereto.

After the research and verification on clinical samples, the method of the disclosure provides very high accuracy in the clinical diagnosis of tumors, therefore has a high clinical value.

The disclosure is further illustrated by the specific examples described below. It should be understood that these examples are merely illustrative, and do not limit the scope of the present disclosure. The experimental methods without specifying the specific conditions in the following examples generally used the conventional conditions, such as those described in J. Sambrook, Molecular Cloning: A Laboratory Manual (3rd ed. *Science Press,* 2002) or followed the manufacturer's recommendation.

Example 1. Tumor Marker CTSM-4F

I. Description of the Sequence for Detection

In this example, the sequence of CTSM-4F tumor marker is shown in the SEQ ID NO: 1, in which the bases in each box are the potential methylated CpG site(s), and the optimal detection region is underlined.

SEQ ID NO: 1 are as follows:

CGCCCAGTAAGTTACGGAAAAGGCGGAGACAGAGGTTTCGTTCC

CGCCCCTCCAATTCAGTCTCCAAAAAGGTCCGCATAATTGATATATA

AGGGGCTTCAGTGTGTAGCAAAGTTGCAAAAGTTAAGAGTTGTTGTTTGT

CTTCGATCATGTCTGGTAGAGGCAAAGGTGGTAAAGGTTTAGGAAAGG

GAGGCGCCAAGCGCCATCGCAAAGTGCTCCGTGACAACATACA

GGGCATCACGAAGCCCGCCATCCGTCGCTTGGCCCGACGCGG

CGCCGTGAAACGCATTTCGGGCCTCATTTATGAGGAGACCCGCG

GTGTTCTTAAGGTGTTCCTGGAGAATGTGATACGGGACGCCGTAA

CCTACACGGAGCACGCCAAGCGTAAGACAGTCACTGCAATGGATG

TTGTCTACGCGCTCAAGCGCCAGGGACGCACTCTGTACGGCTTT

GGTGGCTGAGCCTCACCCCGGCTTTTTATTTAACAGCTCACCCATAAA

AGGCCCTTTTCAGGGCCACCTCCTTCGTCACACGAAGGGCTGTAAC

TGATGACGACTTGGGTTTCGTTTTGTAAATTTGGGATTCTAACTGA

GTTAAACCGAGCCGTTTTTAGCGATCTTCCTAAGATGGCGGAT

GTGCTAAGGAGAAAGGGAAGGCGAAACATTAGAAACTTGTTCAGGTAT

TTCGATCGCAAACATT

II. Detection Step

1. Obtaining samples: selecting clinical tissue samples, including cancer tissue and corresponding paracarcinoma control tissue.

2. DNA extraction: extracting the genomic DNA of the sample by conventional phenol-chloroform method.

3. DNA methylation was detected by pyrosequencing as follows:

(1) Bisulfite treatment: 5-200 ng above extracted genomic DNA was treated with bisulfate using Methylation-Gold™ Kit (ZYMO Research, Cat. No. D5006) according to its instruction, and finally eluted with 20 ul eluent and used as the template for subsequent PCR amplification.

(2) SEQ ID NO: 2 was obtained after bisulfate treatment, wherein Y represents C (cytosine) or T (thymine). As compared with SEQ ID NO: 1, the original methylated cytosine C remains unchanged, but the original unmethylated cytosine is converted to T (U), therefor Y is used to represent C or T.

SEQ ID NO: 2 are as follows:

YGTTTAGTAAGTTAYGGAAAAGGYGGAGATAGAGGTTTYGTTTTYGTTTTT

TTAATTTAGTTTTTAAAAAGGTTYGTATAATTGATATATTAAGGGGTTTTAGTGTG

TAGTAAAGTTGTAAAAGTTAAGAGTTGTTGTTTGTTTTYGATTATGTTTGGTAGA

-continued

GGTAAAGGTGGTAAAGGTTTAGGAAAGGGGAGCYGTTAACYGTTATYGTAAAG

TGTTG YGTGATAATATATAGGGTATTA YGAAGTT YGYGTTATT YGYGT YGYGTTTGGTTY

GAYGYGCYGCYGTGAAAYGTATTTYGGGTTTTATTTATGAGGAGATTYGYGGT

GTTTTTAAGGTGTTTTTGGAGAATGTGATAYGGGAYGTYGTAATTTATAYGGAG

TAYGTTAACYGTAAGATAGTTATTGTAATGGATGTTGTTTAYGYGTTTAACYGT

TAGGGAYGTATTTTGTAYGGTTTTGGTGGTTGAGTTTTATTTYGGTTTTTTATTA

ATAGTTTATTTATAAAAGGTTTTTTTTAGGGTTATTTTTTTYGTTATAYGAAGGGT

TGTAATTGATGAYGATTTGGGTTTYGTTTTGTAAATTTGGGATTTTAATTGAGTT

AAATYGAGTYGTTTTTACYGATTTTTTTAAGATGCYGGATGTGTTAAGGAGAAA

GGGAAGCYGAAATATTAGAAATTTGTTTAGGTATTTYGATYGTAAATATT

Based on SEQ ID NO: 2 and the characteristics of nested PCR and pyrosequencing, sets of amplification primers and sequencing primers were designed, as shown in Table 1 (corresponding to the sequence shown underlined or in bold in the SEQ ID NO: 2):

TABLE 1

| | Primer Name | Primer sequence |
|---|---|---|
| First run PCR | CTSM-4F-F1 | GTAGAGGTAAAGGTGGTAAAGGTTTAG (SEQ ID NO: 9) |
| | CTSM-4F-R1 | *aaccttcaacaccccaaccatata*AAAACACCRCRAATCTCCTCATAAAT (SEQ ID NO: 10) |
| Second run PCR | CTSM-4F-F2 | TGTTGYGTGATAATATATAGGGTATT (SEQ ID NO: 11) |
| | CTSM-4F-R2 (biotin modified at 5' terminal) | aaccttcaacaccccaaccatata (SEQ ID NO: 12) (corresponding to the lowercase and italicized part of CTSM-4F-R1) |

(3) Nested PCR: using 2×PCR Master Mix (Lifefeng Biotech Co., Ltd, Cat No. PT102), but not limited thereto.

Amplification system of the first run of PCR was as follows:

| Component | Volume |
|---|---|
| 2 × PCR Mix | 5 ul |
| CTSM-4F-F1 (10 uM) | 0.1 ul |
| CTSM-4F-R1 (10 uM) | 0.1 ul |
| Template | 1 ul |
| $ddH_2O$ | 3.8 ul |

Amplification procedure of the first run of PCR was as follows:

| | | |
|---|---|---|
| Pre-denaturation | 98° C. | 30 s |
| Amplification of 30 cycles | 98° C. | 10 s |
| | 58° C. | 30 s |
| | 72° C. | 30 s |
| Extension | 72° C. | 3 min |
| Preservation | 4° C. | |

After the first run of PCR, its products were used as templates for the second run of PCR. The amplification system of the second run of PCR was as follows:

| | |
|---|---|
| 2 × PCR Mix | 13 ul |
| CTSM-4F-F2 (10 uM) | 0.5 ul |
| CTSM-4F-R2 (biotin modified at 5' terminal) (10 uM) | 0.5 ul |
| Template | 4 ul |
| $ddH_2O$ | 12 ul |

Amplification procedure of the second run of PCR was as follows:

| | | |
|---|---|---|
| Pre-denaturation | 98° C. | 30 s |
| Amplification of 30 cycles | 98° C. | 10 s |
| | 58° C. | 30 s |
| | 72° C. | 30 s |
| Extension | 72° C. | 3 min |
| Preservation | 4° C. | |

(4) Agarose gel electrophoresis: to identify the specificity of PCR products, the length of the amplified product was detected by agarose gel electrophoresis, which should be 177 bp.

(5) Pyrosequencing: the methylation value of each CpG site in the target region was detected through the pyrosequencing instrument (QIAGEN) according to the steps in the instruction.

(6) Analysis and calculation: the methylation values of 11 CpG sites were detected by pyrosequencing, and their average value was calculated as the final methylation value of the sample in this region. Although the average value is used here, other calculation such as sum or median of the methylation values can be used.

III. Result

By analyzing the methylation values of samples, the tumor samples can be effectively distinguished from the control samples. CTSM-4F is hypomethylated in the control samples, while in the tumor samples, CTSM-4F is hypermethylated.

IV. Clinical Detection and Analysis

1. Detection and Analysis of Rectal Cancer

Among the confirmed rectal cancer samples obtained from the hospital, 4 cases of colorectal cancer samples were randomly selected, and the corresponding paracarcinoma tissues were used as control samples.

Using the above methods of II to IV, the DNA from these samples was obtained and subjected to bisulfite treatment, nested PCR, agarose gel electrophoresis, pyrosequencing, and analysis and calculation of the methylation values of CpG sites.

As shown in FIG. 1, results indicated that the methylation level of CTSM-4F in control samples was significantly lower than that in colorectal cancer samples, and CTSM-4F was significantly abnormal hypermethylated in colorectal cancer, which can be used as an excellent marker for colorectal cancer. Further expansion of the clinical samples showed the same significance.

2. Detection and Analysis of Liver Cancer

Among the confirmed liver cancer samples obtained from the hospital, 8 cases of liver cancer samples were randomly selected, and the corresponding paracarcinoma tissues were used as control samples.

Using the above methods of II to IV, DNA was obtained from these samples and subjected to bisulfite treatment, nested PCR, agarose gel electrophoresis, pyrosequencing, and analysis and calculation of the methylation value of CpG sites.

Figure 2:
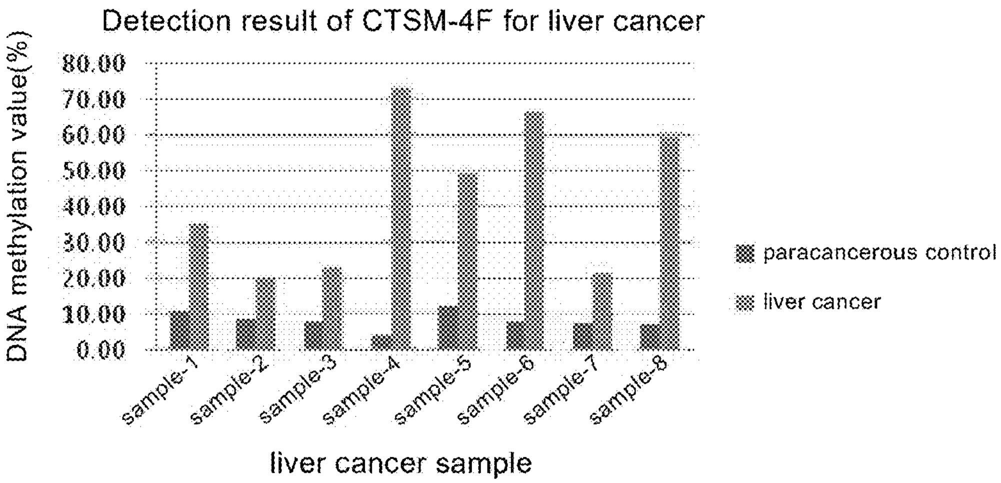
FIG. 2. Detection results of CTSM-4F for liver cancer.

As shown in FIG. 2, results indicated that the methylation level of CTSM-4F in control samples was significantly lower than that in liver cancer samples, and CTSM-4F was significantly abnormal hypermethylated in liver cancer, which can be used as an excellent marker for liver cancer. Further expansion of the clinical samples showed the same significance.

3. Detection and Analysis of Head and Neck Tumor

Among the confirmed head and neck tumor samples obtained from the hospital, 5 cases of head and neck tumor samples were randomly selected, and the corresponding paracarcinoma tissues were used as control samples.

Using the above methods of II to IV, DNA was obtained from these samples and subjected to bisulfite treatment, nested PCR, agarose gel electrophoresis, pyrosequencing, and analysis and calculation of the methylation value of CpG sites.

Figure 3:
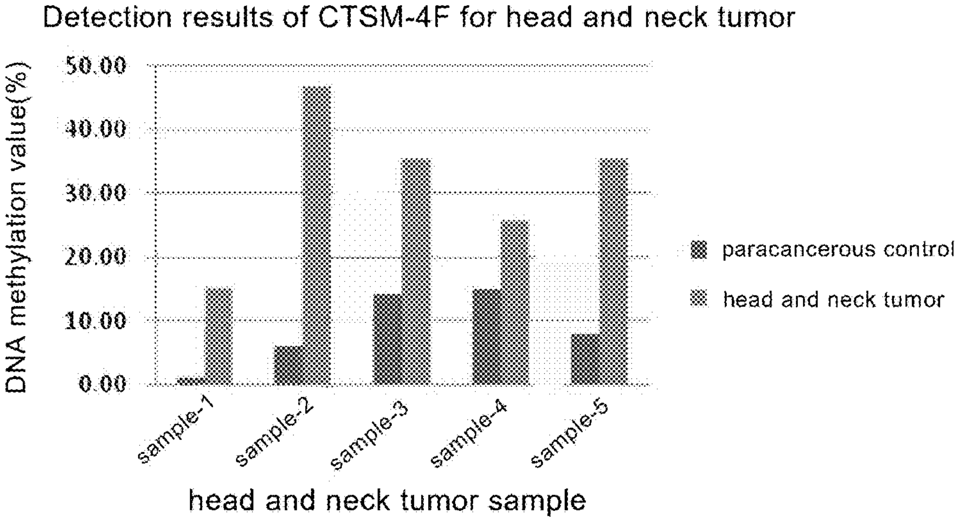
FIG. 3. Detection results of CTSM-4F for head and neck tumor.

As shown in FIG. 3, results indicated that the methylation level of CTSM-4F in control samples was significantly lower than that in head and neck tumor samples, and CTSM-4F was significantly abnormal hypermethylated in head and neck tumor, which can be used as an excellent marker for head and neck tumor. Further expansion of the clinical samples showed the same significance.

4. Detection and Analysis of Lung Cancer

Among the confirmed lung cancer samples obtained from the hospital, 5 cases of lung cancer plasma samples were randomly selected as the experimental group, and 5 cases of normal plasma samples were selected as the control group.

Using the above methods of II to IV, DNA was obtained from these samples and subjected to bisulfite treatment, nested PCR, agarose gel electrophoresis, pyrosequencing, and analysis and calculation of the methylation value of CpG sites.

Figure 4:
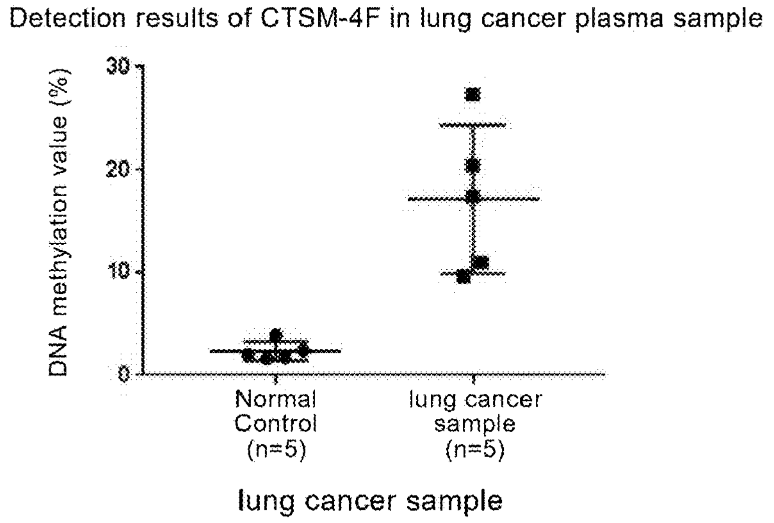
FIG. 4. Detection results of CTSM-4F for lung cancer.

As shown in FIG. 4, results indicated that the methylation level of CTSM-4F of the control group was significantly lower than that of the experimental group, and CTSM-4F was significantly abnormal hypermethylated in lung cancer, which can be used as an excellent marker for lung cancer. Further expansion of the clinical samples showed the same significance.

Example 2. Tumor Marker CTSM-2BE

I. Description of the Sequence for Detection

In this example, the sequence of CTSM-2BE tumor marker is shown in the SEQ ID NO: 3, in which the bases in each box are the potential methylated CpG site(s). The optimal detection region is underlined.

```
SEQ ID NO: 3 are as follows:
AGCTGTTTGTTAAATAGGCTTTCATTTTAATTTTTTAAAAAATATTTTCA

CTAGTTAGACGGAATATTTATTTCTGATCCTCGTTGTAGGGCTAAAC

TAGGTGTGACTTGCTTTTCCATTAAGGACTGTAGCCATTTTGGCTAAGAA

AGTCTTTCCTGTCTTAGCTCTCTTCAAGAGATGCTATTTACTTTTTTGTT

GTTGTTTTCTCCGGAGCTTTATTGCCTACCCTTTATTTTCACGATGT

GTTTGTGCATTCTGTAAAAAGTGGGAAACACTGTTCTCCGGATTGTGT

GGGTGATCGCCGGTCGCCTAGCTTGCCGTTCTTCAGGTATCTC

CTGCTGCTCCAGAATCTACATCTGAATGTCAAGGCATAGCTTTTCCAGGA

GCTTTTAAACCGACCTTTCAATTCGAAGACGTAACTCCGCCAG

GAGCTTTGTCTCCCTGGCATATAAAAGCATAGAAGAGAGCAACTTCTGGT

TTTTAAAATAAGTAAACTAATCTGAATTGTTTGCAATGGTAGGAACTTGT

TATATAAAATGTTAATTAGGTGGCCCGTGCTCGAAAACTGCTCTCAG

GATATGACCAATGGGAGAGTAGACCTAAGCTCCTTCATTTGCATGCAGA
```

SEQ ID NO: 4 was obtained after bisulfate treatment, wherein Y represents C (cytosine) or T (thymine).

```
SEQ ID NO: 4 are as follows:
AGTTGTTTGTTAAATAGGTTTTTATTTTAATTTTTTAAAAAATATTTTTA

TTAGTTAGAYGGAATATTTATTTTTGATTTTYGTTGTAGGGTTAAAT

TAGGTGTGATTTGTTTTTTTATTAAGGATTGTAGTTATTTTGGTTAAGAA

AGTTTTTTTTGTTTTAGTTTTTTTTAAGAGATGTTATTTATTTTTTTGTT

GTTGTTTTTTTYGGAGTTTTATTGTTTATTTTTTATTTTTAYG

ATGTGTTTGTGTATTTTGTAAAAAGTGGGAAATATTGTTTTTYG
```

-continued

```
GATTGTGTGGGTGATYGTYGGTYGTTTAGTTTGTYGTTTTTTAG

GTATTTTTTGTTGTTTTAGAATTTATATTTGAATGTTAAGGTATAGTTTT

TTTAGGAGTTTTTAAATYGATTTTTTAATTYGAAGAYGTAATTG

YGTTAGGAGTTTTGTTTTTTTGGTATATAAAAGTATAGAAGAGAGTAA

TTTTTGGTTTTTAAAATAAGTAAATTAATTTGAATTGTTTGTAATGGTAG

GAATTTGTTATATAAAATGTTAATTAGGTGGTTYGTGTTYGAAAATT

GTTTTTAGGATATGATTAATGGGAGAGTAGATTTAAGTTTTTTTATTTGT

ATGTAGA
```

Based on SEQ ID NO: 4 and the characteristics of nested PCR and pyrosequencing, sets of amplification primers and sequencing primers were designed and showed in Table 2.

TABLE 2

| | Primer Name | Primer sequence |
|---|---|---|
| First run PCR | CTSM-2BE-F1 | GATGTGTTTGTGTATTTTGTAAAAAGTG(SEQ ID NO: 13) |
| | CTSM-2BE-R1 | aaccttcaacaccccaaccatataTATACCTTAACATTCAAATATAAATTC(SEQ ID NO: 14) |
| Second run PCR | CTSM-2BE-F2 | TTTTYGYGGATTGTGTGGGTGA(SEQ ID NO: 15) |
| | CTSM-2BE-R2 (biotin modified at 5' terminal) | aaccttcaacaccccaaccatata(SEQ ID NO: 12) |

By use of the same methods as Example 1 and the above primers, DNA was extracted from samples and subjected to bisulfite treatment, nested PCR, agarose gel electrophoresis, pyrosequencing, and analysis and calculation of the methylation value of CpG sites.

II. Clinical Detection and Analysis

1. Detection and Analysis of Breast Cancer

Among the confirmed breast cancer samples obtained from the hospital, 8 cases of breast cancer samples were randomly selected, and the corresponding paracarcinoma tissues were used as control samples.

DNA was obtained from these samples and subjected to bisulfite treatment, nested PCR, agarose gel electrophoresis, pyrosequencing, and analysis and calculation of the methylation value of CpG sites.

Figure 5:
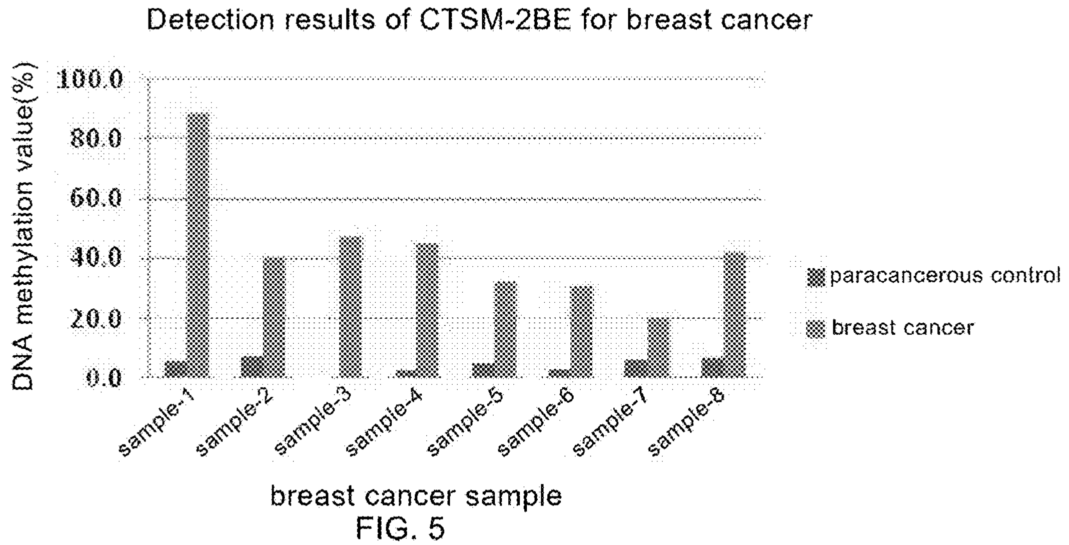
FIG. 5. Detection results of CTSM-4F for breast cancer.

As shown in FIG. 5, results indicated that the methylation level of CTSM-2BE in control samples was significantly lower than that in breast cancer samples, and CTSM-2BE was significantly abnormal hypermethylated in breast cancer, which can be used as an excellent marker for breast cancer. Further expansion of the clinical samples showed the same significance.

2. Detection and Analysis of Head and Neck Tumor

Among the confirmed head and neck tumor samples obtained from the hospital, 6 cases of head and neck tumor samples were randomly selected, and the corresponding paracarcinoma tissues were used as control samples.

DNA was obtained from these samples and subjected to bisulfite treatment, nested PCR, agarose gel electrophoresis, pyrosequencing, and analysis and calculation of the methylation value of CpG sites.

Figure 6:
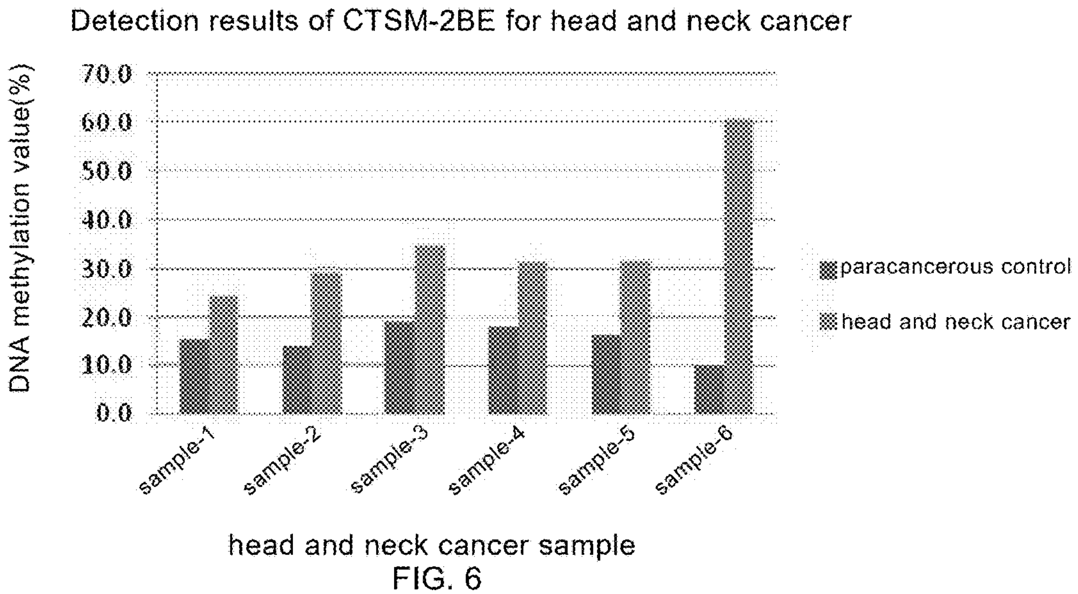
FIG. 6. Detection results of CTSM-2BE for head and neck cancer.

As shown in FIG. 6, results indicated that the methylation level of CTSM-2BE in control samples was significantly lower than that in head and neck tumor samples, and CTSM-2BE was significantly abnormal hypermethylated in head and neck tumor, which can be used as an excellent marker for head and neck tumor. Further expansion of the clinical samples showed the same significance.

3. Detection and Analysis of Lung Cancer

Among the confirmed lung cancer samples obtained from the hospital, 8 cases of lung cancer samples were randomly selected, and the corresponding paracarcinoma tissues were used as control samples.

DNA was obtained from these samples and subjected to bisulfite treatment, nested PCR, agarose gel electrophoresis, pyrosequencing, and analysis and calculation of the methylation value of CpG sites.

Figure 7:
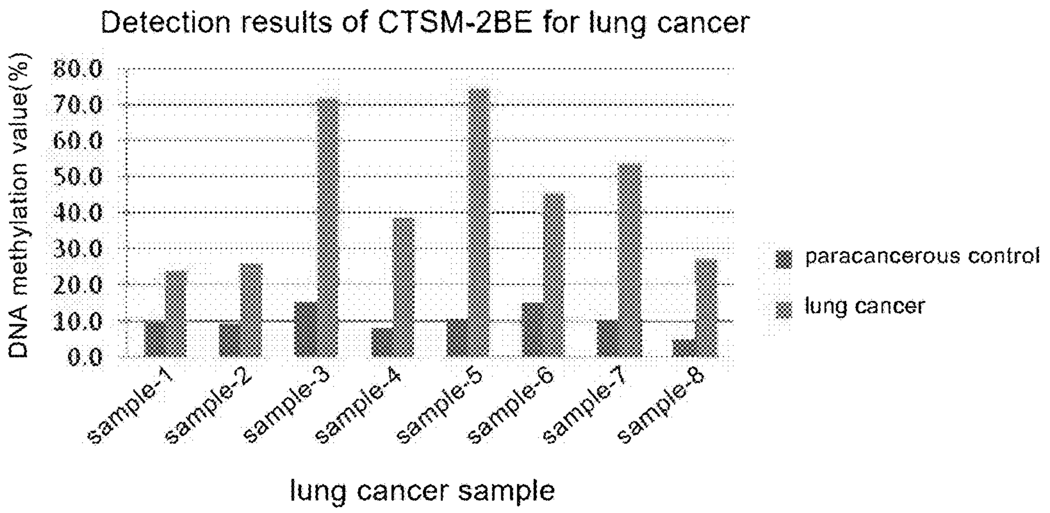
FIG. 7. Detection results of CTSM-2BE for lung cancer.

As shown in FIG. 7, results indicated that the methylation level of CTSM-2BE in control samples was significantly lower than that in lung cancer samples, and CTSM-2BE was significantly abnormal hypermethylated in lung cancer, which can be used as an excellent marker for lung cancer. Further expansion of the clinical samples showed the same significance.

4. Detection and Analysis of Pancreatic Cancer

Among the confirmed pancreatic cancer samples obtained from the hospital, 8 cases of pancreatic cancer samples were randomly selected, and the corresponding paracarcinoma tissues were used as control samples.

DNA was obtained from these samples and subjected to bisulfite treatment, nested PCR, agarose gel electrophoresis, pyrosequencing, and analysis and calculation of the methylation value of CpG sites.

Figure 8:
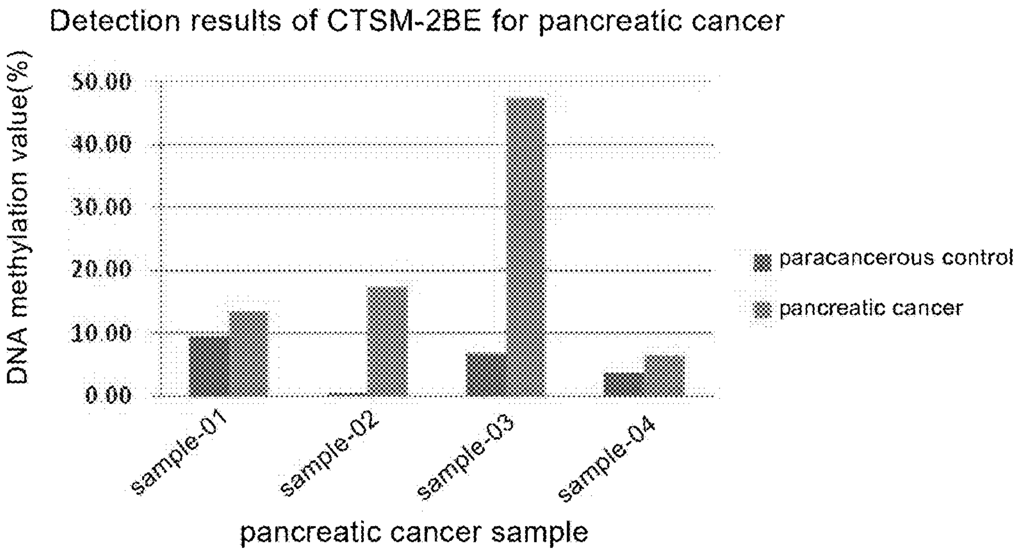
FIG. 8. Detection results of CTSM-2BE for pancreatic cancer.

As shown in FIG. 8, results indicated that the methylation level of CTSM-2BE in control samples was significantly lower than that in pancreatic cancer samples, and CTSM-2BE was significantly abnormal hypermethylated in pancreatic cancer, which can be used as an excellent marker for pancreatic cancer. Further expansion of the clinical samples showed the same significance.

Example 3. Tumor Marker CTSM-3C

I. Description of the Detection Sequence

In this example, the sequence of CTSM-3C tumor marker is shown in the SEQ ID NO: 5, in which the bases in each box are the potential methylated CpG site(s). The optimal detection region is underlined.

SEQ ID NO: 5 are as follows:

TGGGGCAACTCATCCAATAAGATTGTCTAGTAATGAACCAATCAGTCTGG

TCACTCTTCAGCCAATGATTTTATCGCGCGGGACTTTTGAAATATTACAG

GACCAATCAGAATGTTTCTCACTATATTTAAAGGCCACTTGCTCTCAGTT

CACTACACTTTTGTGTGTGCTCTCATTGCAAATGGCTCGTACGAAGCAAA

CAGCTCGCAAGTCTACCGGCGGCAAAGCTCCGCGCAAGCAGCTTGCTACT

ACTAAAGCAGCCCGTAAGAGCGCTCCGGCCACCGGTGGCGTGAAGAAACCT

CATCGCTACCGCCCGGGCACCGTGGCCTTGCGCGAAATCCGTCGTCCAGA

AGTCCACCGAGCTGCTGATCCGGAAGCTGCCGTTCCAGCGCCTGGTGCGA

GAAATCGCCCAGGACTTCAAAACCGACCTGCGTTTCCAGAGCTCTGCGGT

GATGGCGCTGCAGGAGGCTTGTGAGGCCTACCTGGTGGGACTCTTCGAAG

ACACCAATCTGTGCGCTATTCACGCTAAACGCGTCACCATCATGCCCAAA

GATATCCAGCTGGCACGTCGCATCCGTGGGGAAAGGGCATAAGTCTGCC

CGTTTCTTCCTCATTGAAAAGGCTCTTTTCAGAGCCACTCACAATTTCAC

TTAAAAACAGTTGTAACCCA

SEQ ID NO: 6 was obtained after bisulfate treatment, wherein Y represents C (cytosine) or T (thymine):

SEQ ID NO: 6 are as follows:

TGGGGTAATTTATTTAATAAGATTGTTTAGTAATGAATTAATTAGTTTGG

TTATTTTTTAGTTAATGATTTTATYGYGYGGGATTTTTGAAATATTATAG

GATTAATTAGAATGTTTTTTATTATATTTAAAGGTTATTTGTTTTTAGTT

TATTATATTTTTGTGTGTGTTTTTATTGTAAATGGTTYGTAYGAAGTAAA

TAGTTYGTAAGTTTATYGGYGGTAAAGTTTYGYGTAAGTAGTTTGTTATT

AAAGTAGTTYGTAAGAGYGTTTYGGTTATYGGYGTGGYGTGAAGAAATTTTA

TYGTTATYGTTYGGGTATYGTGGTTTTGYGYGAAATTYGTYGTTATTAGA

AGTTTATYGAGTTGTTGATTYGGAAGTTGTYGTTTTAGYGTTTGGTGYGA

GAAATYGTTTAGGATTTTAAAATYGATTTGYGTTTTTAGAGTTTTGYGGT

GATGGYGTTGTAGGAGGTTTGTGAGGTTTATTTGGTGGGATTTTTYGAAG

ATATTAATTTGTGYGTTATTTAYGTTAAAYGYGTTATTATTATGTTTAAA

GATATTAGTTGGTAYGTYGTATTYGTGGGGAAAGGGTATAAGTTTGTT

YGTTTTTTTTTTATTGAAAAGGTTTTTTTTAGAGTTATTTATAATTTTAT

TTAAAAATAGTTGTAATTTA

Based on SEQ ID NO: 6 and the characteristics of nested PCR and pyrosequencing, sets of amplification primers and sequencing primers are designed and showed in Table 3.

TABLE 3

| | Primer Name | Primer sequence |
|---|---|---|
| First run PCR | CTSM-3C-F1 | TTTGTTTTTAGTTTATTATATTTTTGTGTG (SEQ ID NO: 16) |
| | CTSM-3C-R1 | aaccttcaacaccccaaccatataAACTACTTTAATAACAAACTACTTAC (SEQ ID NO: 17) |
| Second run PCR | CTSM-3C-F2 | GTGTGTGTTTTTATTGTAAATGG (SEQ ID NO: 18) |
| | CTSM-3C-R2 (biotin modified at 5' terminal) | Aaccttcaacaccccaaccatata (SEQ ID NO: 12) |

By use of the same methods as Example 1 and the above primers, DNA was extracted from samples and subjected to bisulfite treatment, nested PCR, agarose gel electrophoresis, pyrosequencing, and analysis and calculation of the methylation value of CpG sites.

II. Clinical Detection and Analysis

1. Detection and Analysis of Colorectal Cancer

Among the confirmed colorectal cancer samples obtained from the hospital, 9 cases of colorectal cancer samples were randomly selected, and the corresponding paracarcinoma tissues were used as control samples.

DNA was obtained from these samples and subjected to bisulfite treatment, nested PCR, agarose gel electrophoresis, pyrosequencing, and analysis and calculation of the methylation value of CpG sites.

Figure 9:
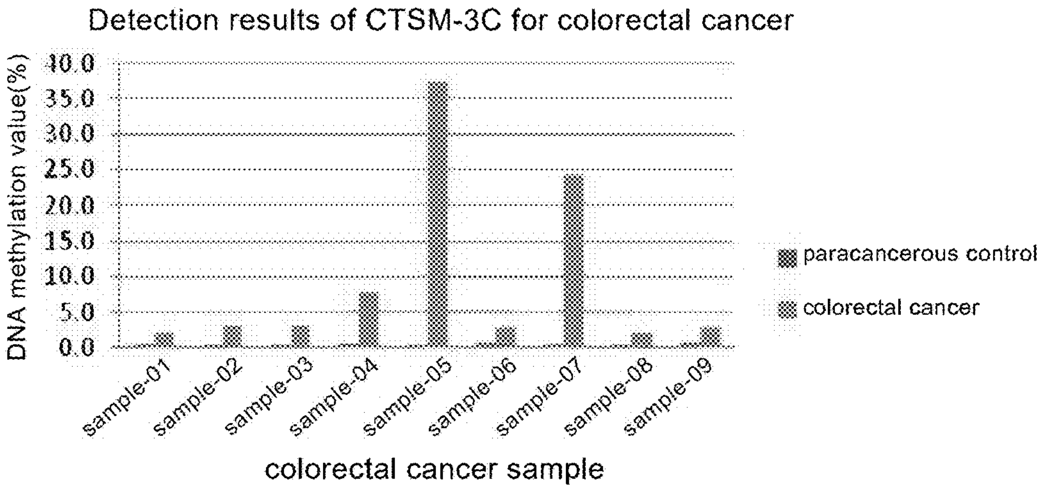
FIG. 9. Detection results of CTSM-3C for colorectal cancer.

As shown in FIG. 9, results indicated that the methylation level of CTSM-3C in control samples was significantly lower than that in colorectal cancer samples, and CTSM-3C was significantly abnormal hypermethylated in colorectal cancer, which can be used as an excellent marker for colorectal cancer. Further expansion of the clinical samples showed the same significance.

2. Detection and Analysis of Head and Neck Cancer

Among the confirmed head and neck cancer samples obtained from the hospital, 5 cases of head and neck cancer samples were randomly selected, and the corresponding paracarcinoma tissues were used as control samples.

DNA was obtained from these samples and subjected to bisulfite treatment, nested PCR, agarose gel electrophoresis, pyrosequencing, and analysis and calculation of the methylation value of CpG sites.

Figure 10:
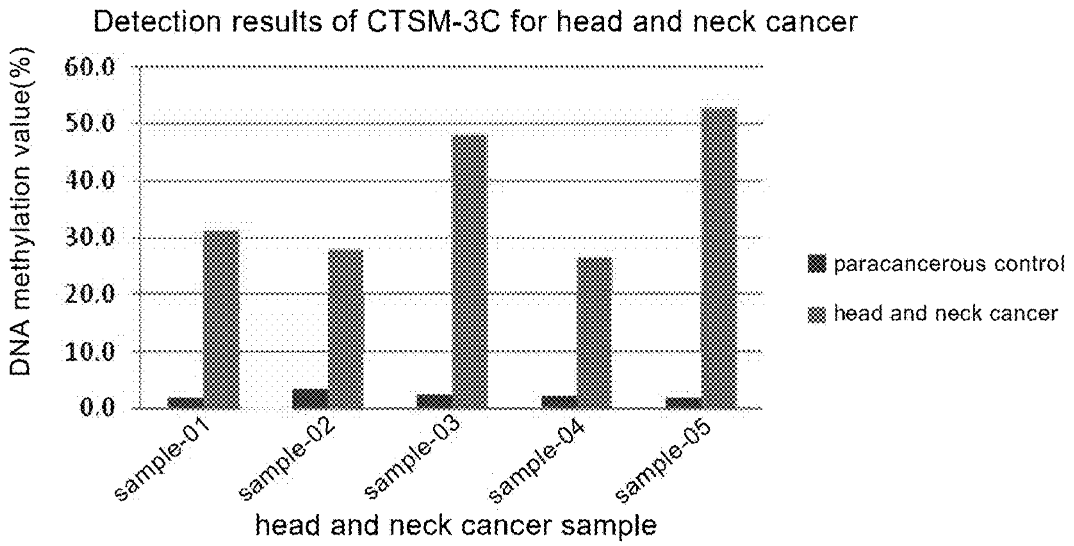
FIG. 10. Detection results of CTSM-3C for head and neck cancer.

As shown in FIG. 10, results indicated that the methylation level of CTSM-3C in control samples was significantly lower than that in head and neck cancer samples, and CTSM-3C was significantly abnormal hypermethylated in head and neck cancer, which can be used as an excellent marker for head and neck cancer. Further expansion of the clinical samples showed the same significance.

3. Detection and Analysis of Lung Cancer

Among the confirmed lung cancer samples obtained from the hospital, 6 cases of lung cancer samples were randomly selected, and the corresponding paracarcinoma tissues were used as control samples.

DNA was obtained from these samples and subjected to bisulfite treatment, nested PCR, agarose gel electrophoresis, pyrosequencing, and analysis and calculation of the methylation value of CpG sites.

Figure 11:
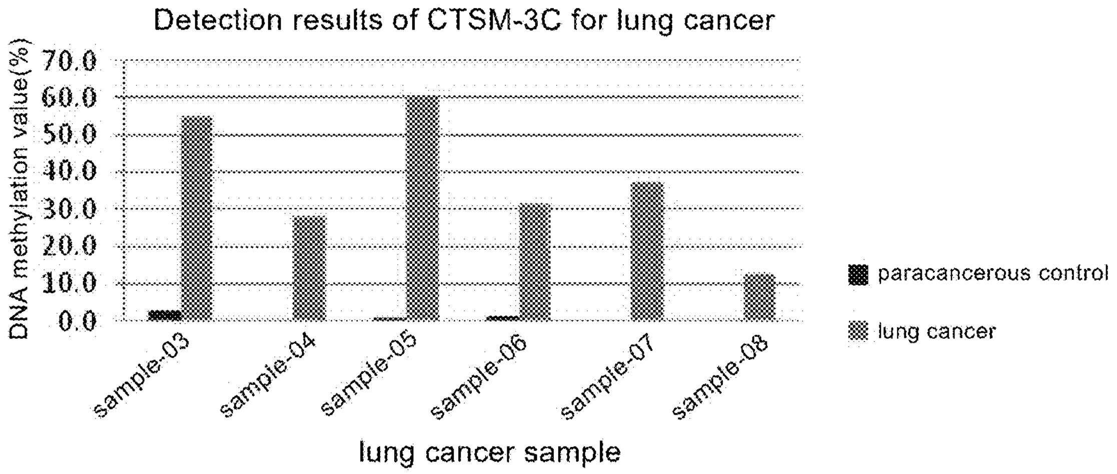
FIG. 11. Detection results of CTSM-3C for lung cancer.

As shown in FIG. 11, results indicated that the methylation level of CTSM-3C in control samples was significantly lower than that in lung cancer samples, and CTSM-3C was significantly abnormal hypermethylated in lung cancer, which can be used as an excellent marker for lung cancer. Further expansion of the clinical samples showed the same significance.

Example 4. Tumor Marker CTSM-4I

I. Description of the Sequence for Detection

In this example, the sequence of CTSM-4I tumor marker is shown in the SEQ ID NO: 7, in which the bases in each box are the potential methylated CpG site(s). The optimal detection region is underlined.

SEQ ID NO: 7 are as follows:

TACCCATAAAAGAAAGCTGCCATCACAGGCAGCAGACCTTTGTTCTCTGA

CCACTTGATAATGTCAGGACGCGCAAAGGAGGTAAGGGCCTGGGGAAAG

GGGGTGCCAAGCGCCACCGCAAGGTGCTGCGCGACAACATCCAGGGTATC

ACCAAGCCAGCCATTCGGCGCCTTGCTCGCCGCGGCGGCGTGAAGCGCAT

TTCTGGCCTCATCTATGAGGAGACCCGCGGAGTGTTGAAGGTGTTCCTGG

AGAACGTGATCCGGGACGCCGTGACCTACACGGAGCACGCCAAGCGCAAG

ACGGTCACCGCCATGGACGTGGTCTACGCGCTCAAGCGCCAGGGCCGCAC

CCTCTATGGCTTCGGCGGCTAAAT

SEQ ID NO: 8 was obtained after bisulfite treatment, wherein Y represents C (cytosine) or T (thymine):

SEQ ID NO: 8 are as follows:
TATTTATAAAAGAAAGTTGTTATTATAGGTAGTAGATTTTTGTTTTTTGA

TTATTTGATAATGTTAGGAYGYGGTAAAGGAGGTAAGGGTTTGGGGAAAG

GGGGTGTTAAGYGTTATYGTAAGGTGTTGYGYGATAATATTTAGGGTATT

ATTAAGTTAGTTATTYGGYGTTTTGTTYGTYGYGGYGGYGTGAAGYG

TATTTTTGGTTTTATTTATGAGGAGATTYGYGGAGTGTTGAAGGTGTTTTTGG

AGAAYGTGATTYGGGAYGTYGTGATTTATAYGGAGTAYGTTAAGYGTAAG

AYGGTTATYGTTATGGAYGTGGTTTAYGYGTTTAAGYGTTAGGGTYGTAT

TTTTTATGGTTTYGGYGGTTAAAT

Based on SEQ ID NO: 8 and the characteristics of nested PCR and pyrosequencing, sets of amplification primers and sequencing primers are designed and showed in Table 4.

TABLE 4

| | Primer Name | Primer sequence |
|---|---|---|
| First run PCR | CTSM-4I-F1 | GGGTGTTAAGYGTTATYGTAAGGTGTTG (SEQ ID NO: 19) |
| | CTSM-4I-R1 | **aaccttcaacaccccaaccatata**CTCCTCATAAATAAAACCAAAAATAC (SEQ ID NO: 20) |
| First run PCR | CTSM-4I-F2 | **TTTAGGGTATTATTAAGTTAGTTA** (SEQ ID NO: 21) |
| | CTSM-4I-R2 (biotin modified at 5' terminal) | aaccttcaacaccccaaccatata (SEQ ID NO: 12) |

II. Clinical Detection and Analysis

1. Detection and Analysis of Breast Cancer

Among the confirmed breast cancer samples obtained from the hospital, 4 cases of breast cancer samples were randomly selected, and the corresponding paracarcinoma tissues were used as control samples.

DNA was obtained from these samples and subjected to bisulfite treatment, nested PCR, agarose gel electrophoresis, pyrosequencing, and analysis and calculation of the methylation value of CpG sites.

Figure 12:
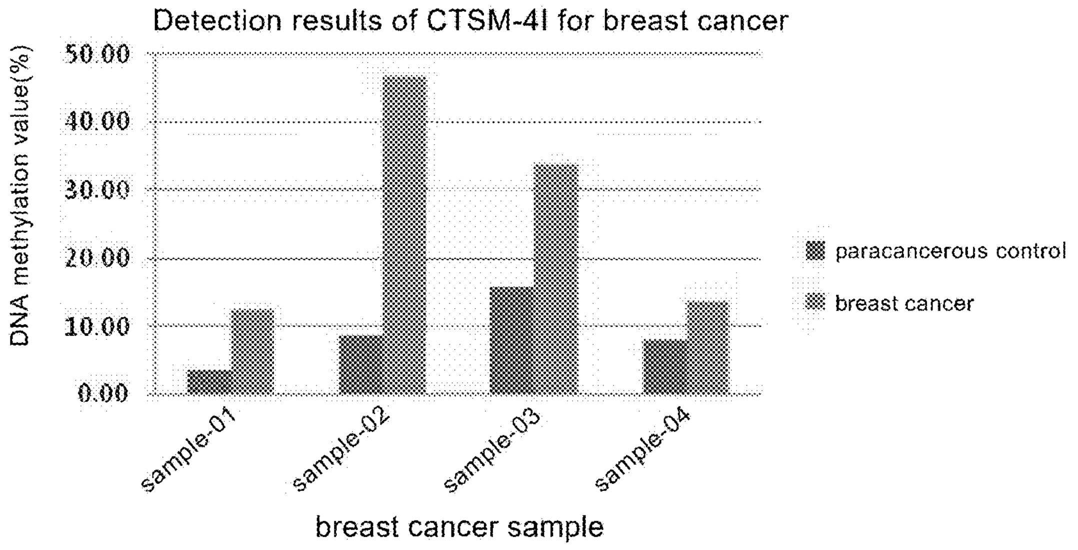
FIG. 12. Detection results of CTSM-4I for breast cancer.

As shown in FIG. 12, results indicated that the methylation level of CTSM-4I in control samples was significantly lower than that in breast cancer samples, and CTSM-4I was significantly abnormal hypermethylated in breast cancer, which can be used as an excellent marker for breast cancer.

2. Detection and Analysis of Colorectal Cancer

Among the confirmed colorectal cancer samples obtained from the hospital, 5 cases of colorectal cancer samples were randomly selected, and the corresponding paracarcinoma tissues were used as control samples.

DNA was obtained from these samples and subjected to bisulfite treatment, nested PCR, agarose gel electrophoresis, pyrosequencing, and analysis and calculation of the methylation value of CpG sites.

Figure 13:
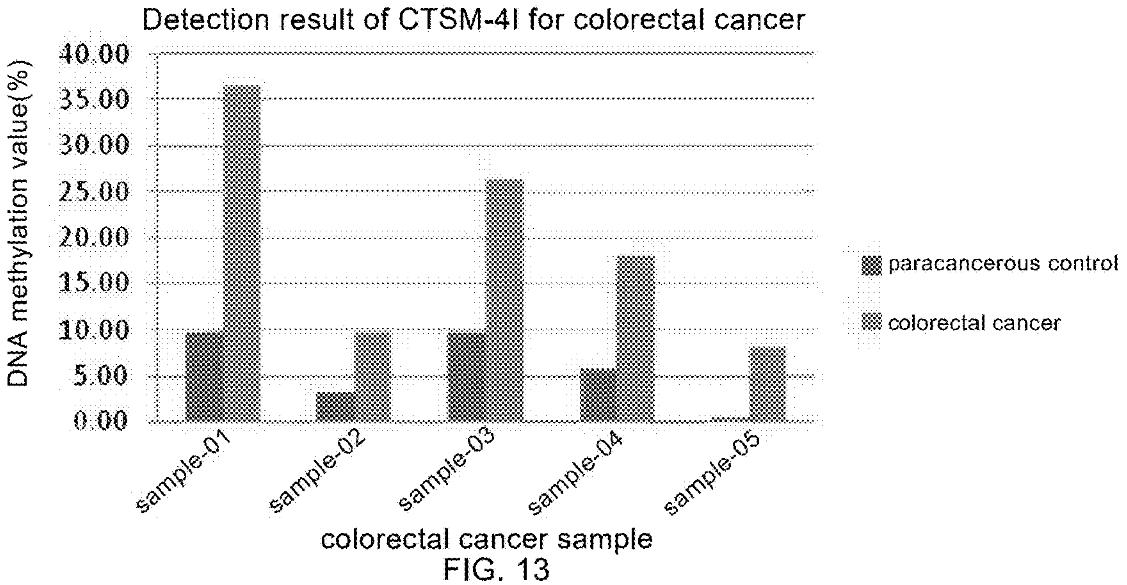
FIG. 13. Detection results of CTSM-4I for colorectal cancer.

As shown in FIG. 13, results indicated that the methylation level of CTSM-4I in control samples was significantly lower than that in colorectal cancer samples, and CTSM-4I was significantly abnormal hypermethylated in colorectal cancer, which can be used as an excellent marker for colorectal cancer.

3. Detection and Analysis of Head and Neck Cancer

Among the confirmed head and neck cancer samples obtained from the hospital, 6 cases of head and neck cancer samples were randomly selected, and the corresponding paracarcinoma tissues were used as control samples.

DNA was obtained from these samples and subjected to bisulfite treatment, nested PCR, agarose gel electrophoresis, pyrosequencing, and analysis and calculation of the methylation value of CpG sites.

Figure 14:
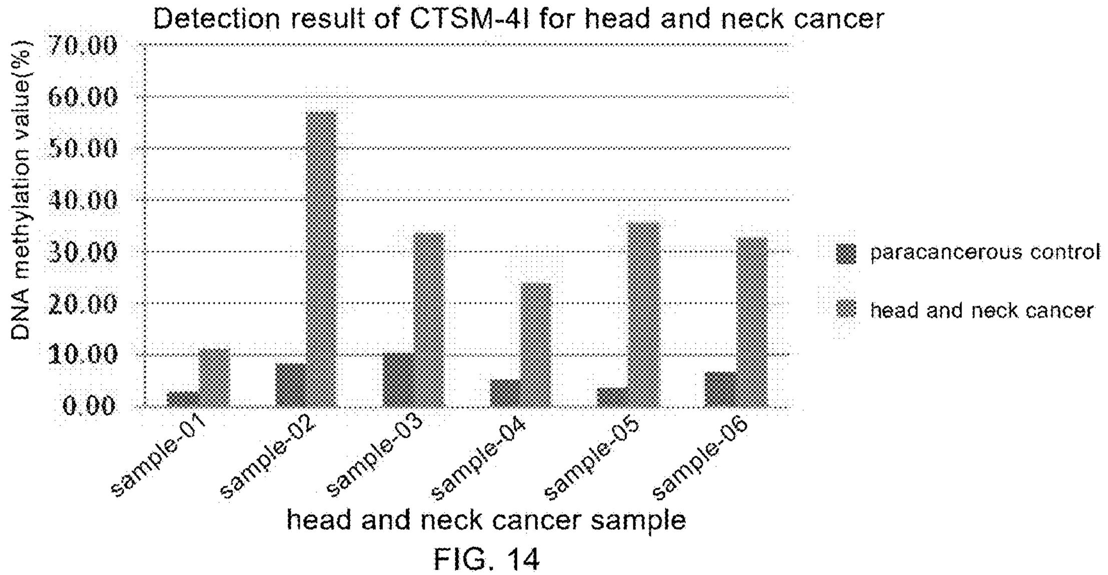
FIG. 14. Detection results of CTSM-4I for head and neck cancer.

As shown in FIG. 14, results indicated that the methylation level of CTSM-4I in control samples was significantly lower than that in head and neck cancer samples, and CTSM-4I was significantly abnormal hypermethylated in head and neck cancer, which can be used as an excellent marker for head and neck cancer. Further expansion of the clinical samples showed the same significance.

4. Detection and Analysis of Lung Cancer

Among the confirmed lung cancer samples obtained from the hospital, 7 cases of lung cancer samples were randomly selected, and the corresponding paracarcinoma tissues were used as control samples.

DNA was obtained from these samples and subjected to bisulfite treatment, nested PCR, agarose gel electrophoresis, pyrosequencing, and analysis and calculation of the methylation value of CpG sites.

Figure 15:
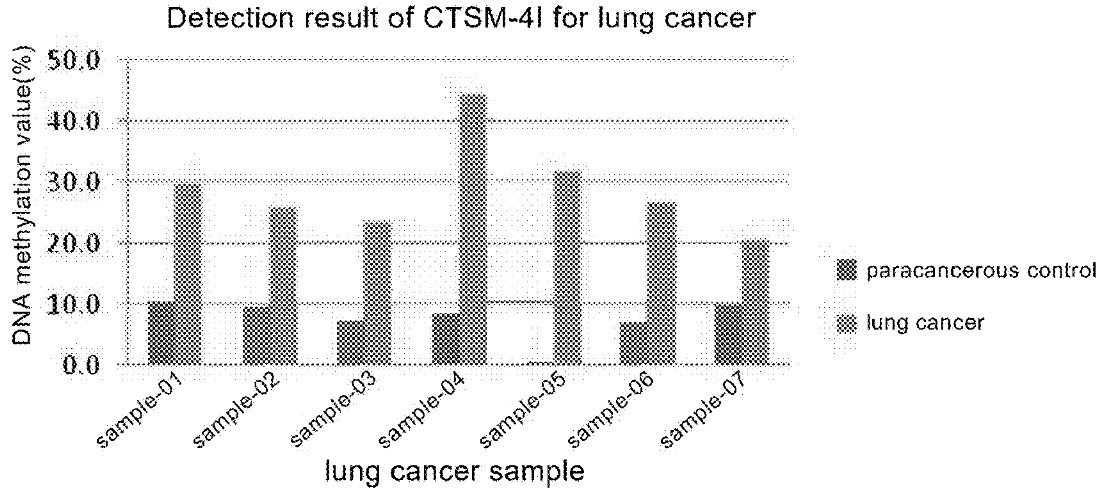
FIG. 15. Detection results of CTSM-4I for lung cancer.

As shown in FIG. 15, results indicated that the methylation level of CTSM-4I in control samples was significantly lower than that in lung cancer samples, and CTSM-4I was significantly abnormal hypermethylated in lung cancer, which can be used as an excellent marker for lung cancer. Further expansion of the clinical samples showed the same significance.

Each reference provided herein is incorporated by reference to the same extent as if each reference was individually incorporated by reference. In addition, it should be understood that based on the above teaching content of the disclosure, those skilled in the art can practice various changes or modifications to the disclosure, and these equivalent forms also fall within the scope of the appended claims.

We claim:

1. A method for detecting one or more tumors in a subject, comprising:

treating DNA extracted from one or more samples comprising tumor cells taken from the subject with a reagent that modifies DNA in a methylation-specific manner;

detecting a modification of a CpG site of a polynucleotide in the DNA extracted from one or more samples using a tumor detection agent or kit;

wherein said polynucleotide is a fragment obtained by amplifying human genomic DNA treated with bisulfite using primers SEQ ID NO: 9-12;

wherein detecting modification of a CpG site of the polynucleotide comprises performing pyrosequencing, bisulfite conversion sequencing, whole genome methylation sequencing, methylation specific PCR, or any combination thereof; and wherein detecting the modification of the CpG site of the polynucleotide indicates the presence of one or more tumors from a group consisting of colorectal cancer, liver cancer, and head and neck cancers.

2. A method of detecting a fragment of SEQ ID NO: 1 in a sample, said fragment comprising residues 240-296 of SEQ ID NO: 1, the method comprising:

(i) providing the sample and extracting genomic DNA from the sample;

(ii) treating the genomic DNA with bisulfite to convert the unmodified cytosine into uracil;

(iii) amplifying the genomic DNA treated with bisulfite using primers SEQ ID NO: 9-12; and (iv) analyzing the amplified human genomic DNA in (iii) to detect methylation of a CpG, wherein the CpG is located between nucleotides 240-296 of SEQ ID NO: 1, and wherein, in step (iv), analyzing comprises performing pyrosequencing, bisulfite conversion sequencing, qPCR, second generation sequencing, whole genome methylation sequencing, DNA enrichment detection, simplified bisulfite sequencing technology, HPLC, or a combination thereof.

* * * * *